United States Patent [19]

Mathieu et al.

[11] Patent Number: 4,514,295
[45] Date of Patent: Apr. 30, 1985

[54] DIALYSIS APPARATUS

[75] Inventors: Bernd Mathieu, Spiesen; Hans-Dietrich Polaschegg, Oberursel, both of Fed. Rep. of Germany

[73] Assignee: Fresenius AG, Bad Homburg, Fed. Rep. of Germany

[21] Appl. No.: 404,557

[22] Filed: Aug. 2, 1982

[30] Foreign Application Priority Data

Aug. 5, 1981 [DE] Fed. Rep. of Germany ....... 3131075

[51] Int. Cl.³ ............................................. B01D 31/00
[52] U.S. Cl. .................................... 210/90; 210/321.3; 604/5
[58] Field of Search ...................... 210/90, 137, 321.3; 138/30; 604/5, 118; 128/DIG. 3

[56] References Cited

U.S. PATENT DOCUMENTS 2,838,073  6/1958  Mattia et al. ........................... 138/30
3,756,234  9/1973  Kopp ......................................... 604/5
4,031,008  6/1977  Anno ..................................... 210/137

FOREIGN PATENT DOCUMENTS 2441210  6/1975  Fed. Rep. of Germany .......... 604/5

Primary Examiner—Frank Spear
Attorney, Agent, or Firm—Omri M. Behr

[57] ABSTRACT

A blood accumulator for use in single needle dialysis systems is provided with elastic walls so that expansion of the accumulator in an outward direction may take place and in the filled condition, the walls are stretched. After the blood input pump is stopped and a valve opened, blood makes its way at a controlled rate out of the accumulator past the dialysis diaphragm back to the patient's body.

17 Claims, 8 Drawing Figures

DIALYSIS APPARATUS

BACKGROUND OF THE INVENTION

The present invention relates to an apparatus for freeing blood of metabolic products and, more especially relates to dialysis with a single connection with the patient's circulatory system, that is to say a single needle dialysis, using a first pipe running away from this connection and a second pipe running towards it, a dialysis diaphragm joined up with these pipes, at least one pump and at least one part with a valve function in at least one of the pipes for controlling the input and output of blood in the circuit outside the patient's body, a blood accumulator forming part of one of the pipes, and an automatic controller for the pump and the part functioning as a valve.

Unlike normal hemodialysis in which the patient's skin and vessels have to be punctured with separate needles for taking the blood from his or her body and running it back thereinto, single needle dialysis makes do with one needle, such dialysis offering the useful effect that the number of punctures is decreased to one half so that, on the one hand, there is less damage to the vessels while on the other hand pain produced on puncturing the skin is cut down. In particular in the case of acute dialysis a single opening into a vessel is all that is needed so that, in cases of emergency, treatment is made much simpler.

However, the shortcoming caused by single needle dialysis is the stop-go turning on and off of the inflow and outflow of blood and the fact that, in part, cleaned blood and uncleaned blood are mixed together at the needle used for joining up the patient with the dialysis apparatus in single needle dialysis.

Unlike continuous dialysis using two needles, in which the pressure within the dialysis system may undergo, generally speaking, adjustment within more or less tight limits, in single needle dialysis an increase and decrease in pressure takes place all the time because of the fact that at any one time blood is being taken up by the apparatus and then later is run off back into the body. For this reason, it is hard to keep to the desired flow rates at a given average pressure in a single needle operation so that attempts have been made at taking care of such shortcomings.

In fact, German Offenlegungsschrift specification No. 2,417,900 relates to a blood dialysis apparatus in which immediately downstream from an y-like needle, whose ends are joined with the arterial and vein pipes, there is a pump, a dialysis diaphragm, and a bubble trap in the vein pipe. In one embodiment, using a further pipe the bubble trap is joined up with a pressure monitor controlling a double clip unit, placed right on the y-like end of the needle, for clipping and shutting off, in one case, the arterial pipe and, in the other case, the vein pipe. In this system there is a pressure-dependent control in a bubble trap with rigid walls, the blood pumped into the trap in fact elastically compressing the air space thereover and, for this reason, activating the pressure monitor which, for its part, is used for controlling the double pipe clip unit.

Such a system has a shortcoming inasfar as the pressure limit monitors or gases, necessary for pressure control, are high in price and likely to get out of order, while on the other hand pressure changes at the dialysis diaphragm have an undesired effect on the flow of liquid through the diaphragm so that a balanced liquid take-up by the dialyzer is made harder or may be stopped completely. Furthermore, with such a pressure control system there will be the danger of aspiration in a backward direction of liquid, which may be possibly contaminated, and of air because the pipe system is not completely air-tight.

German Offenlegungsschrift specification No. 2,636,290 is directed to an apparatus for controlling and monitoring blood flow in dialysis in which, in place of the bubble trap as noted, there is a measuring space with, once again, stiff side walls with sensors within them for the purpose of controlling the volume of blood within such measuring space so as to keep to a value somewhere between upper and lower limiting values. At its top end, this measuring space has a unit for evening out pressure, as for example a sterile filter, a bag or a bladder so that, generally speaking, the complete measuring space is freed of pressure. Because of this pressureless condition, this known system has to have two pumps, that is to say one for the input and the other for the output of blood upstream and downstream from the dialysis diaphragm. The use of hose clips, which would be very much cheaper than using a pump, is not possible for this reason, so that the price of making such a dialysis apparatus is very much higher. A further factor going into the price of the apparatus is that vacuum has to be provided at the dialysis diaphragm itself on its dialysate side by a special unit for taking the liquid from the patient at the desired rate.

Such shortcomings could be avoided by a suggestion which has been made in the British Medical Journal, Vol. 281 (1980), page 1109. This paper suggests the use of a single needle dialysis system in which there is a blood input pump in the arterial pipe, running towards the dialysis diaphragm, a flexible accumulator and a blood output pump, there only being one pipe clip on the vein pipe for shutting and opening the pipe. In the operation of the system, in the first place, the accumulator is first pumped full by the one pump without any building up of pressure therein. After turning off this pump, the other pump is turned on and, at the same time, the pipe clip on the vein pipe is opened. The blood in the accumulator is pumped back past the dialysis diaphragm through the vein pipe to the patient, pressure changes in this system being kept down to less than 10 mm Hg. Because no pressure is produced on filling up the accumulator, a second pump is necessarily needed for pumping the blood through the dialysis system. Furthermore, the transdiaphragm pressure adjustment at the dialysis diaphragm has to be controlled from the outside, thus greatly increasing the price of the apparatus and making its operation complex.

GENERAL OUTLINE OF THE INVENTION

For this reason, one purpose of the present invention is providing an apparatus of the sort noted above in which not only pressure, but furthermore volume control are possible.

A further purpose of the invention is providing such an apparatus which requires only a single pump.

A still further purpose of the present invention is to provide such a system which keeps a generally unchanging pressure at the dialysis diaphragm as the blood makes its way therealong, if pressure control is used.

For effecting these purposes, and further puroses, the accumulator has a wall which may be outwardly elastically stretched or, put differently, is such that its circumference may undergo elastic expansion.

As part of the present invention, an accumulator is used whose wall is designed for elastic expansion so that the overall volume within the accumulator may be increased many times. Because of such elastic expansion there is an increase in pressure in the accumulator acting on the amount of blood which has made its way into the accumulator, such pressure being dependent on the volume of the blood within the accumulator.

The way in which changes in pressure take place is naturally dependent on the length and cross-section of the pressure accumulator and, more especially, on its wall thickness. Normally, an accumulator with the desired size may undergo a twenty-fold increase in volume without there being any sharp or steep increase in pressure which would be responsible for the accumulator bursting. The curve representative of the increase in pressure will be such that the pressure, after keeping to a value of zero as the accumulator is being filled up without any wall expansion, will take a sharp upward turn when a small amount of blood is forced into the accumulator and will then go to a value in which there will be hardly any further increase all the time there is an increase in volume, for example a twenty-fold increase, in the amount of blood or the pressure value may even keep to a generally unchanging level. However, once the volume has been increased past this point, there will be a sharp increase in pressure even on pumping in a little more blood. On the one hand such an accumulator for blood under pressure may readily be monitored because the upper and lower pressure values are exceeded in an upward or downward direction because of the pressure/volume curve noted even when there is only a small change in volume near the ends of the range so that, for this reason, pressure control is made very much simpler. For this reason, the average value control of pressure as used in other single needle apparatus is unnecessary. Furthermore, in the leveled-off pressure range there will be an amount of blood which is within a generally equal pressure range so that the blood head at the dialysis diaphragm will be generally equal and so on irregularities are to be feared while dialysis is taking place.

Furthermore, such a single needle system requires only one pump in place of two pumps, the accumulator being in fact a pressure accumulator from which the blood is forced and which only has to be filled up with the use of a pump, the outflow of blood from the accumulator being controlled by way of a pipe clip.

Because there is a great increase in the volume of the accumulator from its starting volume as blood is forced thereinto, the accumulator volume may readily be controlled for example by optical or by mechanical control units. Such a controller may be used, when desired, for pressure control or in a place of a pressure controller.

The accumulator of the present invention is a low-price structure which may for example, be made of widely used latex hose so that the accumulator may be quite easily produced. Furthermore, the accumulator may be readily sterilized and may be produced and marketed in conjunction with a normal dialysis pipe system product.

LIST OF FIGURES AND DETAILED ACCOUNT OF WORKING EXAMPLES OF THE INVENTION

Further details, useful effects and working examples of the invention will be seen in the account now to be given using the figures.

Figure 1:
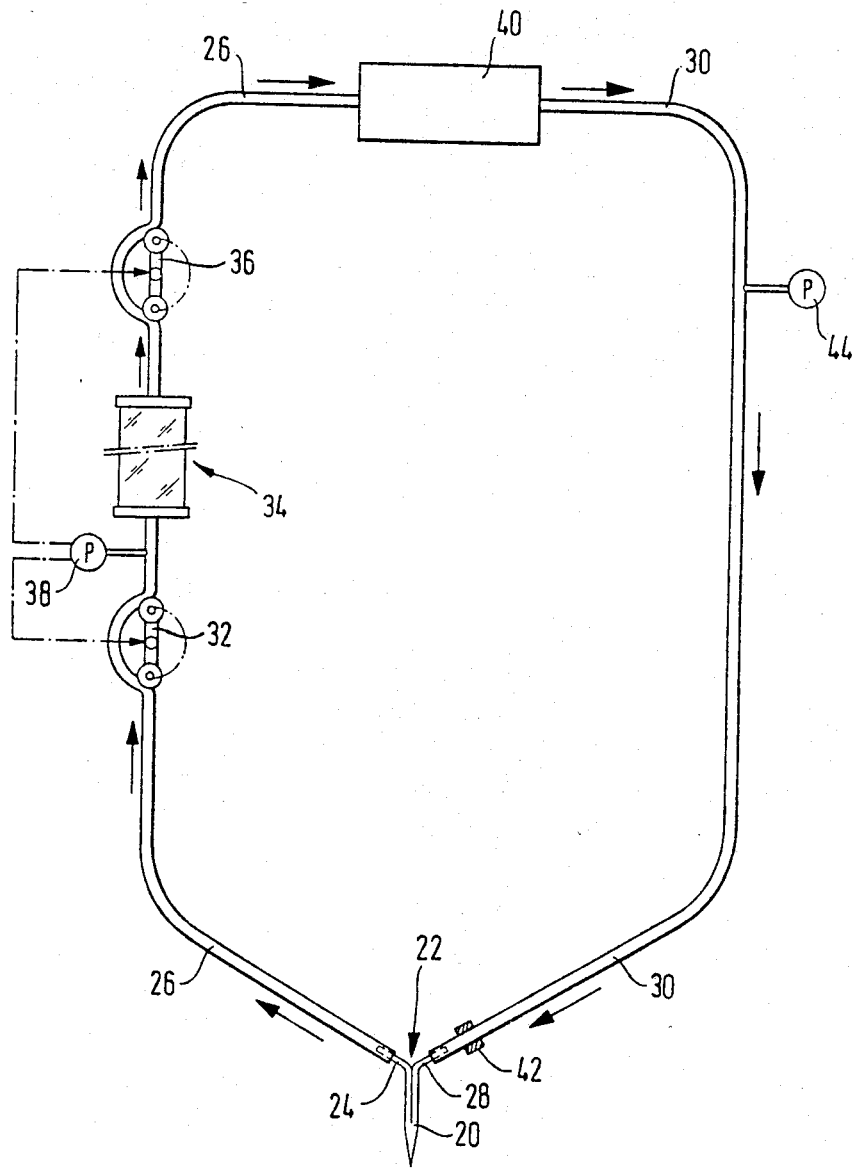
FIG. 1 is a diagrammatic view of a single needle dialysis apparatus with the accumulator of the present invention.

Using the apparatus shown diagrammatically in FIG. 1, blood is taken from a patient by way of a hollow needle 20 pushed through the wall of a blood vessel. At its outer end hollow needle 20 is branched like a letter y at 22, one branch 24 being joined up with an arterial pipe 26, whereas the other branch 28 is joined up with a vein pipe 30. The hollow needle 20 may be in the form of a biflow needle, that is to say it is made up of two hollow needles placed coaxially one within the other and with the outer needle set back by some millimeters for stopping any mixing effect. On the other hand, however, any such low mixing effect may be tolerated when using the conventional y-like needle 20 illustrated herein.

In arterial pipe 26 blood is withdrawn from the y-like hollow needle 20 by a pump 32, suitably in the form of a peristaltic pump, whose output is provided to accumulator 34 by arterial pipe 26, in which blood transported by pump 32 may be stored for the time being. Downstream from accumulator 34 there is, in this first working example of the invention, a second pump 36, which is put into operation on pump 32 being turned off.

There is furthermore within the arterial pipe 26 a sensor 38 placed between pump 32 and the second pump 36, the output signal of such sensor 38 being used for changing over between operation of the first and second pumps 32 and 36. Such a sensor is best designed in the form of a pressure sensor.

Downstream from the second pump 36, the arterial pipe is joined up with the dialysis diaphragm unit 40, within which the blood is freed of metabolic products and excess liquid.

The cleaned blood goes back by way of vein pipe 30 to one branch 28 of hollow needle 20. The vein pipe 30 may be shut at a point near branch 28 by a pipe clip 42 for the purpose of stopping aspiration of blood out of vein pipe 30 when pump 32 is working.

Furthermore, a pressure sensor 44 may be placed in vein pipe 30 for giving a reading for the pressure in the part of the pipe 30 between pump 36 and pipe clip 42.

ACCOUNT OF OPERATION OF THE FIRST WORKING EXAMPLE OF THE INVENTION

Aspiration of blood takes place by way of the hollow needle 20 using pump 32, with pipe clip 42 and the pump 36, (which is responsible for a valve function in addition to a pumping one) shut, in the one case, and turned off, in the other. Because of this, accumulator 34, in the form of a flexible pipe, will firstly necessarily be filled up with blood without any fluid head, but thereafter there will be a sharp increase in pressure because of the stretching of its walls much like the effect on blowing up a balloon. In fact, only a small (further) amount of blood has to be forced into the accumulator to bring this jump in pressure to a levelled-off part of the pressure/volume curve, there only being a small increase along such levelled-off part of the curve as further blood is forced into the accumulator 34. A sharp increase in pressure or pressure jump later occurs when approaching a limiting condition in which there is a change in the elastic properties of the wall of the accumulator.

To keep accumulator 34 from bursting, there is—as we have seen earlier—a sensor 38 between the first pump 32 and the second pump 36, such sensor being a pressure sensor in the present working example of the invention and being used for turning off pump 32 at a certain pressure level and, at the same time, turning on pump 36 and opening pipe clip 42 so that the blood in accumulator 34 is completely pumped out of it over the dialysis diaphragm 40 into the vein pipe 30 and formed there, by way of hollow needle 20, back into the body of the patient. When the pressure within the vein pipe 30 goes under a certain value, as may be sensed for example by the pressure sensor 44 or the sensor 38, pump 36 is turned off and pipe clip 42 shut. Pump 32 is turned on again so that the events take place again.

ACCOUNT OF FURTHER PARTS OF THE INVENTION

Figure 2:
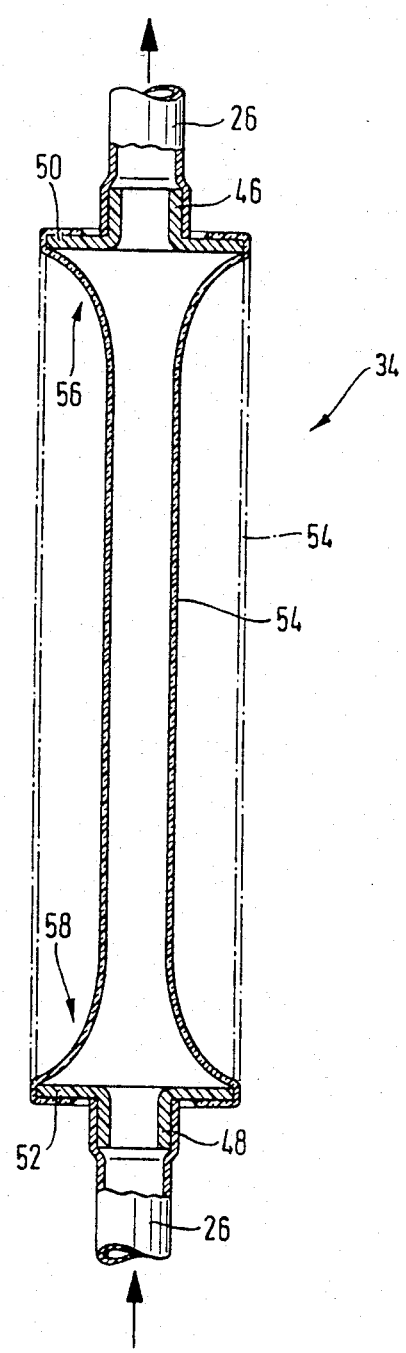
FIG. 2 is a longitudinal cross sectional view of a first working example of the accumulator of the invention.

FIG. 2 is a longitudinal cross sectional view of the first working example of the accumulator 34 used in the invention. Said accumulator 34 has spigots 46 and 48 at its two ends onto which separate lengths of the arterial pipe 26, which will normally be made of flexible synthetic resin, are slipped and fixed in position. Spigot 46 and spigot 48 may be placed in a support (not figured) for the dialysis apparatus and fixed in position there. Spigots 46 and 48 are, in each case, fixed to a plate 50, 52 which should preferably be round. Between plates 50 and 52 there is the accumulator structure 54 in the more limited sense of the word and which is preferably made of elastic hose. In the working example to be seen in FIG. 2, in the accumulator structure 54, a pulling force is applied at its end parts 56 and 58 to pull them out to a somewhat greater width to make it possible for said ends to be slipped over round plates 50 and 52, on which they are fixed, for example, by adhesive or by mechanical clips so that there is no chance of loss of blood out of the accumulator. It will be seen that in this working example of the invention the cross-sectional area of the accumulator structure 54 is a little less than the area of plates 50 and 52, although this does not have to be so in every case. Such areas might in fact be equal or it might even be possible for the cross-sectional area of the accumulator structure 54 to be greater than the areas of plates 50 and 52.

Because of its highly elastic properties, the accumulator structure 54 will be collapsed when not pulled tight so that it may be completely evacuated when acted upon by a low degree of vaccum. And in this first working example of the accumulator 34, it is necessary for the spigots 46 and 48 to be fixed to a further part of the dialysis apparatus, there being in fact some chance of accumulator structure 54 changing its position, if this is not done.

The accumulator structure 54 may be made of highly elastic materials such as for example organic polymers and mixtures thereof such as polyurethanes, forms of neoprene, rubbers, silicone rubbers, latex, rubber, regenerated rubber etc., of which the best material is latex which may, if desired, contain normal additives and materials for stepping up elasticity. Such a hose may undergo a five-fold increase in its volume and may even undergo a ten-fold expansion so that, at least in the preferred working example of the invention, it may take up ten times as much blood as it is able to take up in the pressureless condition.

The wall thickness of such a hose will be in a range of about 0.05 to 0.5 and, more specially, in a range of 0.1 to 0.4 mm. The wall thickness will be made dependent on the desired pressure/volume curve and the desired increase in volume of the present accumulator 34. The thicker the wall of accumulator structure 54, the higher the pressure needed in the first place necessary to allow an increase in volume up to a levelled-off part of such pressure/volume curve. Furthermore, the wall thickness may be such that the levelled-off part of the curve or plateau is at a pressure higher than the pressure in the vein and, in fact, more than 20 mm Hg. Indeed, such a pressure has to be produced in the vein pipe before any blood at all may be forced back into the vein.

The hose volume and the length thereof may be changed in a way geared to the purpose and the design of the dialysis apparatus: Normally, the diameter of such hose will be within a range of 5 to 15 and more especially will have a value of 8 mm, while the length of the hose will be 10 to 20 and preferably 15 cm, although, however, smaller or greater sizes would be possible in as far as this would be in line with the desired purpose. If only small blood volumes are to be pumped, the accumulator will be proportionately smaller in size using a smaller hose than is the case with higher blood throughputs.

A generally flat, levelled-off part of the pressure/volume curve after the sharp increase in pressure may best be produced by the wall thickness of the hose being generally equal along its full length, see the working example of FIG. 2.

Figure 3:
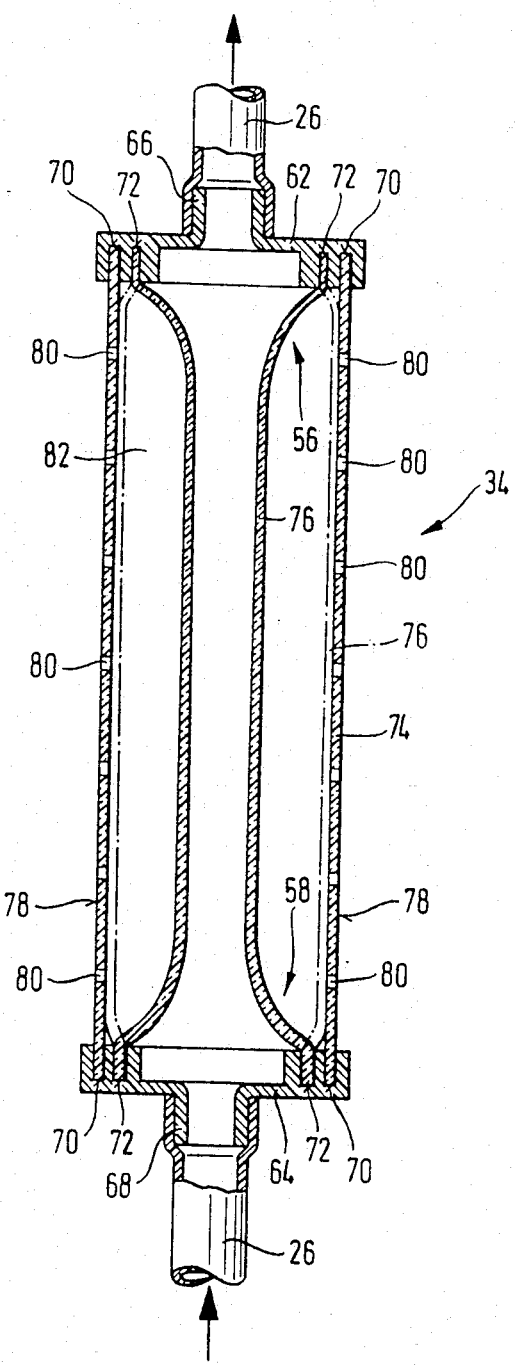
FIG. 3 is a longitudinal cross sectional view of a second working example of the accumulator of the invention.

FIG. 3 is a view of a further working example of the invention in which the wall thickness of the hose of accumulator structure 76 undergoes a generally smooth increase along the full length of the hose. One way of making such a hose is that of lowering a rod into liquid latex material and then pulling it out of the latex material again so that, because of the liquid condition of the latex material, there will be a flow of the part of the material sticking to the rod in a downward direction, the wall thickness of the pipe so produced undergoing a smooth increase from one pipe end to the other. Because of this there is, again, a smooth increase in pressure in the levelled-off or straight part of the curve after the sharp increase at the beginning of the curve.

In the working sample to be seen in FIG. 3 of the accumulator 34 of the invention, the accumulator structure 76 is fixed in position between two plates 62 and 64 which, again, have spigots (66 and 68) for the arterial pipe 26. In the inwardly turned faces of plates there are two ring-like grooves 70 and 72, groove 70 having a stiff pipe 74 forced into it whose cross-sectional is markedly greater than the cross-section of the inner hose 76 or accumulator structure, the same being taken up and fitted into the second inner groove 72. The outer pipe and the hose may, as noted earlier, be fixed by the use of an adhesive or by mechanically fixing.

Inner accumulator structure 76 is, like the accumulator structure 54 of the first working example of the accumulator 34, stretched out at its ends so that it may be taken up in inner groove 72. Between the inner hose or accumulator structure 76 and the stiff outer pipe 74, there is an air space 82 from which air may be let off, suitably through a hole 80 running through the wall 78 of pipe 34 so that there will be no cushioning pressure otherwise stopping an expansion of the accumulator structure 76 in space 82. It is best to have more than one hole 80 through the wall 78 of pipe 74.

If there is only one hole 80, however, and an accumulator structure 76 has a changing wall thickness, such hole 80 in the accumulator structure 64 will be through a part thereof next to a part of hose 76 which has the greatest wall thickness, in veiw of the fact that expansion of the accumulator structure 74 takes place here last.

However, a useful effect may be produced if there is no way of letting off pressure from space 82, that is to say without having any holes in the stiff pipe 74. This makes it possible, on the one hand, for the accumulator structure 76 to be completely evacuated when there is no blood therein so that it is completely collapsed with the outcome that there will be a counter pressure even in the first stage of filling up of the accumulator structure 76. By having, in addition, an elastic air cushion, shut off within space 82, the elasticity of the accumulator 34 will be increased, this being an effect of special value in many cases.

It is best for the selection of the size of pipe 74 to be such that a space 82 has a volume of about 50 to 80 ml, while the volume of the elastic accumulator structure 76 is about 10 to 15 ml in the pressureless condition.

Furthermore, it is to be noted that any water-proof materials may be used for the elastic accumulator structure 54 or 76 which have great enough stretchability (greater than 200%), the materials noted earlier coming within this group of materials.

When, in this working example of the invention, blood is pumped into accumulator structure 76 and pump 36 is turned off, there will, in the first place, only be a small increase in pressure, the accumulator structure becoming full with a very low degree of stretch, the volume only going up by a small amount with only a small increase in volume, blowing up of the accumulator structure 76 being limited to one position till it is resting against the outer pipe 74. The bulge of the accumlator structure formed on expansion will be moved in an axial direction as far as the end of pipe 74, the air present in space 82 being forced out by way of opening 80. On motion of the expansion of accumulator structure in the axial direction, the pressure on the blood to be pumped in will be kept at generally the same level if the wall thickness of the accumulator structure 76 is generally equal. This causes the generally unchanging, levelled-off part of the curve as noted earlier.

When space 82 is completely filled up by accumulator structure 76, which is thus touching the inner wall of pipe 74, there will be a very sharp increase in pressure because the pipe 74 is inelastic.

At this point, operation of pump 36 is started by the one sensor 38, said sensor 38 turning off pump 32 at the same time so that the blood which has made its way into the accumulator structure 76 is run out of it again into the vein pipe 30. Upon the pressure dropping below a predetermined value, which for example may be fixed by the sensor 44, this group of events is stopped and pump 32 put into operation again.

Figure 4:
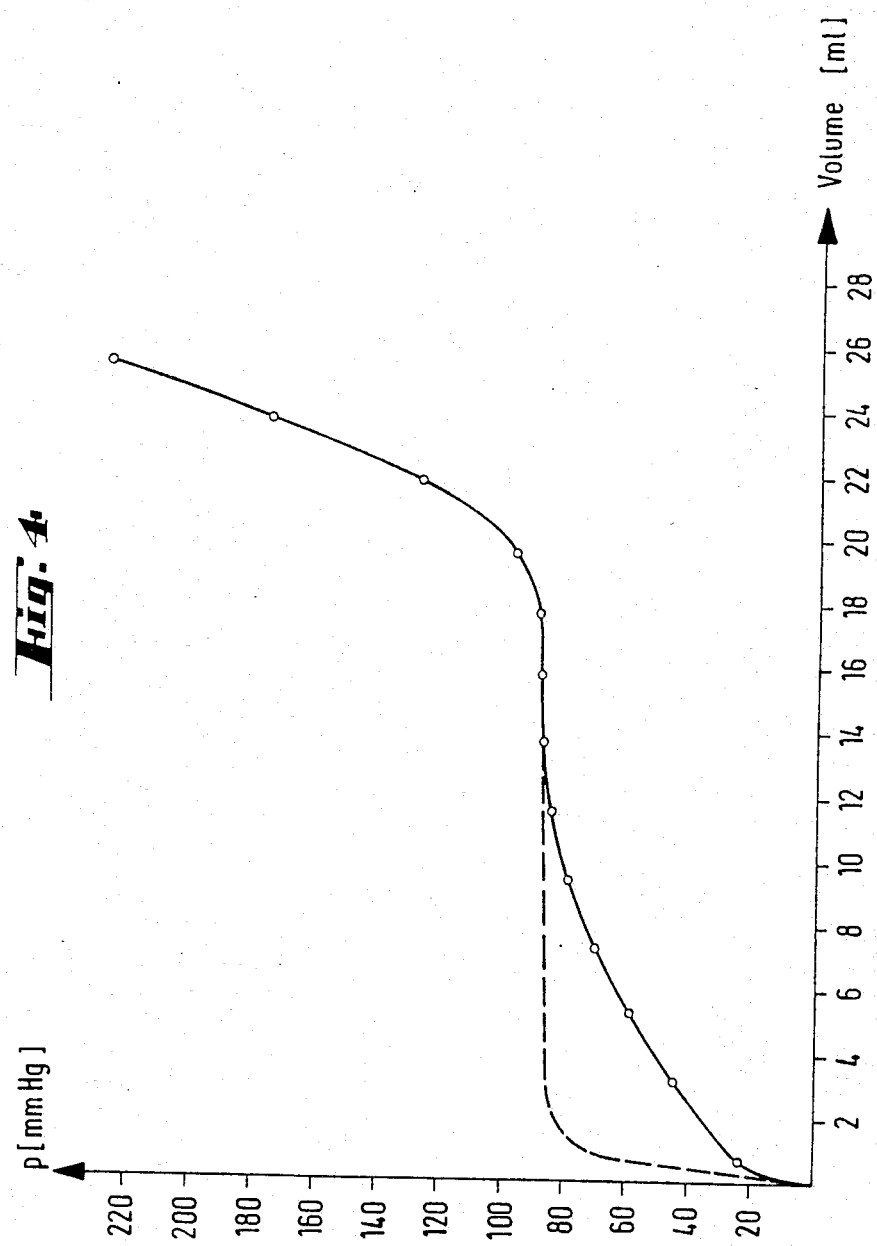
FIG. 4 is a curve representative of the relation between p (pressure) and volume in the working example of the invention to be seen in FIG. 3 on filling with blood.

FIG. 4 is a view of the pressure/volume curve of one example of this second working example of the accumulator, as marked in an unbroken line, whereas the broken line is representative of the best-possible property of an accumulator structure 76 with an even or equal wall thickness. The graph is naturally on the footing of the blood volume being pumped into an accumulator structure 76 as filled up at normal pressure. The accumulator structure to be seen in FIG. 4 has been produced by lowering a rod into a latex bath and then slowly pulling the rod out of it, this being made clear by the smoothly increasing pressure curve in a way dependent on the volume of the blood supplied.

Because the pressure and furthermore the volume figures undergo changes in the elastic accumulator structure 54 and 76, these two readings (pressure and volume) may be used separately from each other, or together, for control of the accumulator 34.

Figure 5:
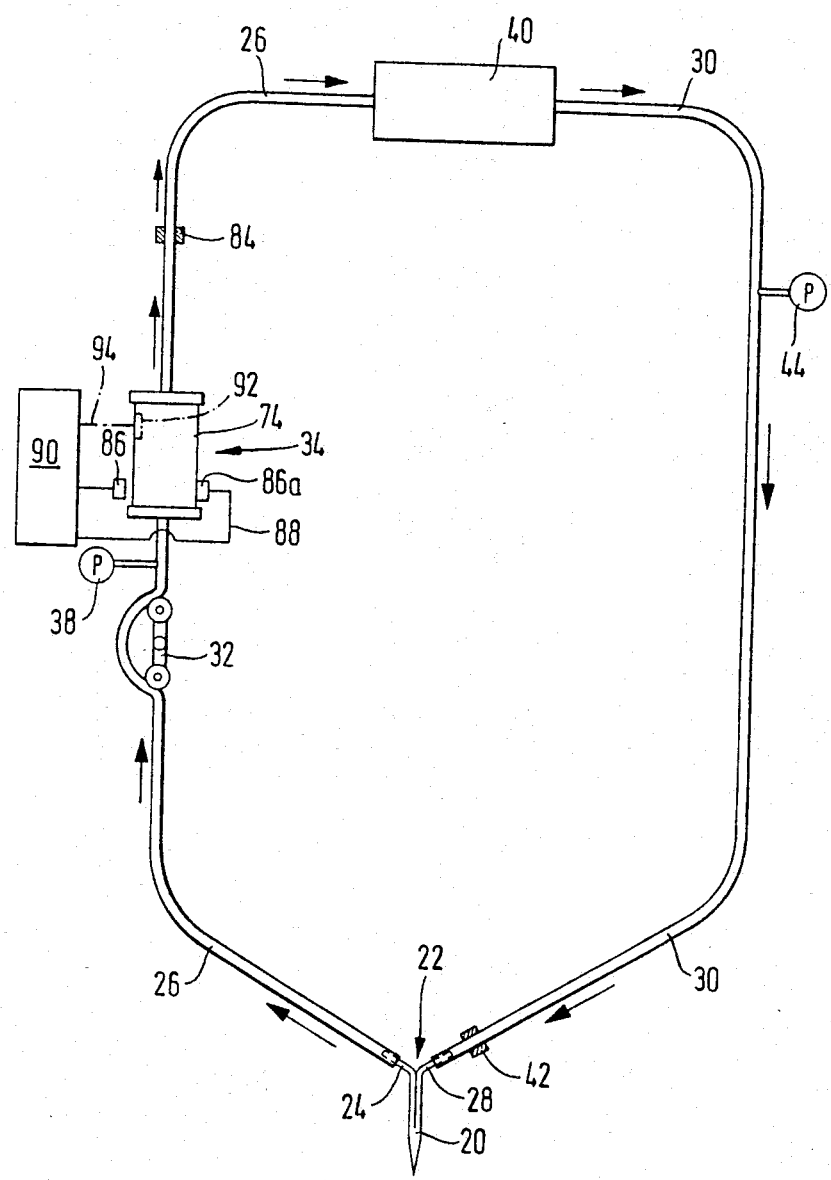
FIG. 5 is a further diagrammatic view of an apparatus for dialysis using the accumulator of the present invention.

FIG. 5 is a view of a special form of the apparatus to be seen in FIG. 1, in which pump 36 has its place taken by a pipe clip 84 which is open if one of the two figures as noted has increased as far as its upper limiting value. This pipe clip 84 may, as desired, have a constant opening cross-section or may, furthermore, have a variable opening cross-section, this being dependent on the amount of blood which is to be let through on operation of the pipe clip. In the case of the levelled-off part of the pressure curve, which is generally unchanging in slope, a pipe clip 84 with a constant opening cross-section will be used to get equal pumping and pressure conditions in the vein pipe 30. On the other hand, in the case of an increasing levelled-off part of the pressure curve, that is to say in the case of pressure and pumping conditions which change while the pipe clip 84 is opened, use may be made of such a clip 84 with a variable opening cross-section in order to keep the rate of pumping through the vein pipe 30 generally equal.

Such a system has the useful effect that the pressure acting on the dialysis diaphragm is not the same as the pump pressure in the accumulator so that the dialysis diaphragm may be used with very much lower pressures, which may be adjusted to be different from the accumulator pressure as may be desired.

The apparatus of FIG. 5 furthermore has optical sensors 86 and 86a placed near the outer edge of the accumulator 34 and more especially on the outer edge of accumulator structure 74, such sensors being joined up by way of a line 88 with a controller 90 for controlling the pipe clips 84 and 42 and the pump 32 by way of lines which are not to be seen in the figure. Such a controller may furthermore be joined up with the sensors 38 and 44. The optical sensors 86 and 86a are so placed near the outer edge of the accumulator structure 74 that the sensor 86, used as a transmitter, sends out radiation into space 82 and the beam so produced is picked up by the sensor 86a used as a detector. This beam is cut off by the expansion of accumulator structure 76, this causing controller 90 to have the effect of turning off pump 32 or terminals 84 and 42.

In a further working example of the invention, the optical sensors 86 and 86a may have their place taken by limit switch 92 which is connected through a line 94 with the controller 90, such switch 92 being, again, fixed on the wall of the pipe 74, and more specially on its inner wall face and is put into operation by way of moving expansion of accumulator structure 76, having the effect of switching limit switch 92.

By using such volume or pressure controls, it is naturally possible for the amount of blood stored in accumulator 34 to be changed as may be desired if the sensors used are adjusted and calibrated for this purpose. It is furthermore possible for a certain amount of blood to be cyclically pumped through the dialysis diaphragm 40, and accumulator 34 not being pumped up till it is completely full.

Accumulator 34 may naturally be placed downstream from the dialysis diaphragm 40, that is to say at the vein pipe 30 and it is furthermore possible for the pump 36 or the pipe clip 84 to be placed as well in and on the vein pipe 30, if this would seem to give a useful effect, without being dependent on the position of the accumulator 34. If pump 32 is kept running all the time and is not turned on and off, a pipe clip, not to be seen in the figure, is placed upstream from it on the arterial pipe 26, such further clip being generally the same as clip 42 and being activated out of phase with clip 42. Furthermore, it is possible to do without clip 42 if the pump 36 is present in the vein pipe 30, pumps 32 and 36 being operated out of phase, that is to say with the one turned off and the other turned on and the other way round. In a special form of the invention, it is possible to have the pump 32 in the arterial pipe and the pipe clip 42 in the vein pipe on the lines of the block circuit diagram to be seen in FIG. 1. Thus pump 36 is not necessary if the accumulator 34 of the present invention is used.

Figure 6:
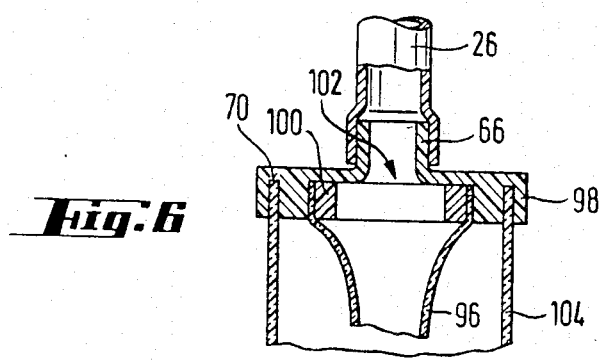
FIG. 6 is a partial longitudinal cross section view of the end of a third working example of the accumulator of the invention.
Figure 7:
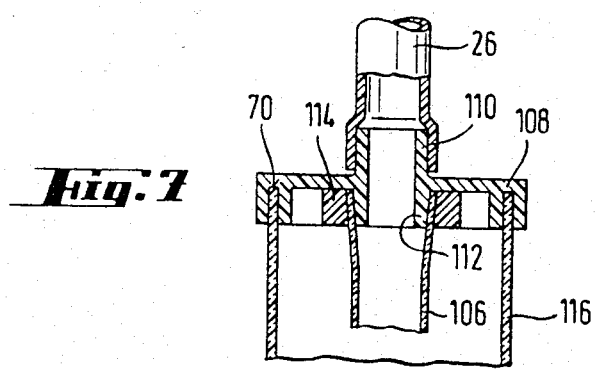
FIG. 7 is a partial longitudinal cross section view of the end part of a fourth working example of the accumulator of the present invention.
Figure 8:
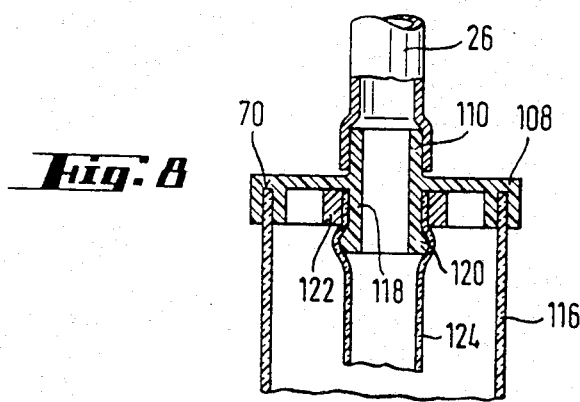
FIG. 8 is a partial longitudinal cross section view of the end part of a fifth working example of the present accumulator.

FIGS. 6 to 8 are views of further working examples of the accumulator of the present invention to specifically illustrate the way of fixing the inflatable flexible pipe or hose on the end plates.

As will be seen from FIG. 6, the inner accumulator structure 96 is fixed on the end plate 98 by using a gripping ring 100 which is preferably cone shaped. It is furthermore best for gripping ring 100 to have a cross-section which is greater than the cross-section of the inner accumulator structure 96 so that it has to be stretched out in a crosswise direction to get it on to the gripping ring. This system is pushed in the end plate 98 or a hollow 102 in the end plate 98, it sticking strongly in position because of the high coefficient of expansion of the material of the holes. Because the inner hose 96 or accumulator structure may be readily stretched in the axial direction, the stiff pipe 104 may readily be slipped into the end plate 98, such operation being undertaken as in the form of the invention to be seen in FIG. 3, which is to be given attention in this respect. In other respects the end plate 98 and the design thereof to be seen in FIG. 6 are the same as the plate 62 and 64 to be seen in FIG. 3.

In FIG. 7 a further way of fixing the inner accumulator structure 106 in position will be seen. In this case the inner plate 108 in the middle has a skirt 112 in line with spigot 110, such skirt becoming narrower in the direction away from plate 108. Accumulator structure 106 is fixed on skirt 112 using a gripping ring 114, in which respect, once again, the system made up of the inner structure 106 and the gripping ring 114 are fittingly placed on skirt 112, the way of fixing the stiff pipe 116 being the same as the way of fixing to be seen in FIG. 6.

In FIG. 8 further forms of the design of FIG. 7 will be seen. Skirt 118 has, at its lower end, an olive or bead 120 whose outer diameter is somewhat greater than the inner diameter of gripping ring 122, the last-named, however, being so elastic that it may be slipped, together with accumulator structure 124, over olive 120 thus to be fixedly kept in position thereby.

It is furthermore best for the accumulator structure to be in an axially stretched condition if the accumulator 34 has the rigid outer pipe 74, 104, 116 or 124, a useful effect being produced if the inner accumulator structure is stretched by at least about 10% of its overall length in the axial direction for stopping any collapse of the accumulator structure. Hand in hand with the stretching in the crosswise or transverse direction, a completely stretched accumulator structure will be produced so that the same may be better inflated with blood on operation and there is the further useful effect of stopping any sticking together of the inner face of the accumulator structure in a collapsed condition when being stored. A further point is that the generally stiff outer pipe 74, 104, 116 or 124 may be used with an accumulator structure or flexible pipe having changing wall thickness and furthermore with one having an equal wall thickness. As a stiff outer structure or body, it is naturally possible to make use of other stiff bodies as for example a piece of netting or like.

We claim:

1. Apparatus for freeing blood of products of metabolism comprising a dialysis diaphragm having a first access means to one side thereof for receipt of blood to be treated and a first outlet means therefrom for the treated blood, a second access means to the other side thereof for the dialysis fluid and a second outflow means therefrom for said fluid, a single connection means for connecting said apparatus to the blood vessel of the patient in need of treatment, a first pipe means for leading blood from said connecting means to said first access means, a second pipe means for connecting said first outflow means back to said single connecting means, valve means in said first and said second pipe means, at least one pump for driving the blood through the apparatus, control means for opening and closing said valve means and controlling said pump means, and an accumulator located in one of said blood pipes, said accumulator comprising a housing having at least one opening therein and a flexible pipe of high elasticity mounted inside said housing having jointing connections at both ends thereof, said opening in said housing providing pressure communication means between the interior of said housing and the atmosphere surrounding said housing.

2. The apparatus as claimed in claim 1, wherein said accumulator has plates at ends thereof, over which ends of the flexible pipe are stretched, each said plate having one of said joining connections.

3. The apparatus as claimed in claim 1 having a generally stiff structure placed round said pipe, said stiff structure having an inner diameter greater than the outer diameter of said flexible pipe so that there is a space of ring-like cross-section between said flexible pipe and said stiff structure, said stiff structure having at least one hole, and plates at the ends thereof.

4. The apparatus as claimed in claim 3, wherein said stiff structure is fixed to said plates at two ends thereof.

5. The apparatus as claimed in claim 3 having sensors for sensing the position of the outer wall of said flexible pipe.

6. The apparatus as claimed in claim 5, wherein said sensors are optical.

7. The apparatus as claimed in claim 5, wherein said sensors are mechanical.

8. The apparatus as claimed in claim 1, wherein said flexible pipe is made of a material with an elongation of at least 200%.

9. The apparatus as claimed in claim 8, wherein said flexible pipe is made of a material selected from the group: polyurethanes, rubbers, silicone rubbers, latex, regenerated rubber or neoprene.

10. The apparatus as claimed in claim 1, wherein said flexible pipe is able to undergo an increase in volume of at least five times.

11. The apparatus as claimed in claim 1, wherein the wall thickness of the flexible pipe is equal generally along its full length.

12. The apparatus as claimed in claim 1, wherein the wall thickness of the pipe undergoes a smooth decrease from one end to the other thereof.

13. The apparatus as claimed in claim 1, wherein the flexible pipe may be caused to undergo an increase in volume at a pressure greater than about 20 mm Hg generally without any further increase being necessary.

14. The apparatus as claimed in claim 1, wherein the flexible pipe is a the condition of axial stretch between said plates.

15. The apparatus as claimed in claim 1, having a clip downstream from said accumulator and said pump is placed upstream from said accumulator.

16. The apparatus as claimed in claim 15, having a control system for operation of said clip as dependent on the pressure in the dialyzer but generally independently of the accumulator pressure.

17. The apparatus as claimed in claim 1 or claim 3, wherein said connection part is a single needle connection part.

* * * * *